(12) United States Patent
Kajii et al.

(10) Patent No.: US 9,017,714 B2
(45) Date of Patent: Apr. 28, 2015

(54) NERVE REGENERATION-INDUCING TUBE

(75) Inventors: Fumihiko Kajii, Ohtsu (JP); Hidenori Tanaka, Ohtsu (JP); Susumu Kashiwabara, Ohtsu (JP); Yuta Kawakatsu, Ohtsu (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 306 days.

(21) Appl. No.: 12/744,609

(22) PCT Filed: Dec. 25, 2008

(86) PCT No.: PCT/JP2008/073554
§ 371 (c)(1),
(2), (4) Date: May 25, 2010

(87) PCT Pub. No.: WO2009/084572
PCT Pub. Date: Jul. 9, 2009

(65) Prior Publication Data
US 2010/0255060 A1      Oct. 7, 2010

(30) Foreign Application Priority Data

Dec. 28, 2007 (JP) ................................. 2007-338902

(51) Int. Cl.
*A61F 2/00*    (2006.01)
*A61L 27/50*   (2006.01)
*A61L 27/34*   (2006.01)
*A61L 27/58*   (2006.01)

(52) U.S. Cl.
CPC ............. *A61L 27/50* (2013.01); *A61L 27/34* (2013.01); *A61L 27/58* (2013.01); *A61L 2430/32* (2013.01)

(58) Field of Classification Search
USPC ...................................................... 424/426
See application file for complete search history.

(56) References Cited

U.S. PATENT DOCUMENTS

| | | | |
|---|---|---|---|
| 4,889,119 A * | 12/1989 | Jamiolkowski et al. | 606/220 |
| 6,090,117 A | 7/2000 | Shimizu | |
| 6,589,257 B1 | 7/2003 | Shimizu | |
| 6,689,166 B2 * | 2/2004 | Laurencin et al. | 623/11.11 |
| 2004/0122454 A1 * | 6/2004 | Wang et al. | 606/152 |
| 2005/0125036 A1 * | 6/2005 | Roby | 606/228 |
| 2005/0161857 A1 * | 7/2005 | Coombes et al. | 264/172.15 |

FOREIGN PATENT DOCUMENTS

| | | | |
|---|---|---|---|
| EP | 0560934 | * | 9/1993 |
| EP | 1 084 686 A1 | | 3/2001 |
| JP | 5-237139 A | | 9/1993 |
| JP | 2002-320630 A | | 11/2002 |
| JP | 2003-19196 A | | 1/2003 |
| JP | 2005-143979 A | | 6/2005 |
| JP | 2005-237476 A | | 9/2005 |
| WO | 95/22301 A1 | | 8/1995 |
| WO | 98/22155 A1 | | 5/1998 |
| WO | 99/63908 A1 | | 12/1999 |

OTHER PUBLICATIONS

Mooney et al. (Biomaterials, vol. 17, pp. 115-124; 1996).*
Matsumoto et al. (Brain Research 868 (2000) 315-328).*
International Search Report of PCT/JP2008/073554, mailing date of Mar. 24, 2009.
European Search Report dated Dec. 20, 2012, issued in corresponding European patent application 08867423.9.
Engelberg, Israel et al., "Physico-mechanical properties of degradable polymers used in medical applications: a comparative study", Biomaterials, vol. 12, No. 3, p. 292-304, Apr. 1, 1991; cited in European Search Report dated Dec. 20, 2012.
Lee, Doug-Youn, "Nerve regeneration with the use of a poly(L-lactide-co-glycolic acid)-coated collagen tube filled with collagen gel", Journal of Cranio-Maxillo-Facial Surgery, vol. 34, No. 1, p. 50-56, Jan. 1, 2006; cited in European Search Report dated Dec. 20, 2012.

* cited by examiner

*Primary Examiner* — David J Blanchard
*Assistant Examiner* — Devang Thakor
(74) *Attorney, Agent, or Firm* — Westerman, Hattori, Daniels & Adrian, LLP

(57) ABSTRACT

A nerve regeneration-inducing tube is provided which is excellent in cell growth property, resistance to pressure, shape recovery property, and anti-kink property in a nerve regeneration-inducing tube where a collagen solution is applied on the outer surface of a tubular body woven with ultrafine fiber comprising biodegradable and bioabsorbable polymer while collagen is filled in the inner area of the tubular body. The nerve regeneration-inducing tube has a degradation speed which is adjusted so as to make it suitable for the connection of nerve gaps of more than 40 mm. The nerve regeneration-inducing tube includes collagen coated on the outer surface of a tubular body woven with fiber bundles where plural ultrafine fibers comprising a biodegradable and bioabsorbable polymer are bundled. The tubular body mostly comprises a first polymer which is biodegradable and bioabsorbable and a second polymer which has higher biodegradability and bioabsorbability than those of the first polymer.

10 Claims, 4 Drawing Sheets

NERVE REGENERATION-INDUCING TUBE

TECHNICAL FIELD OF THE INVENTION

The present invention relates to a method for the manufacture of a nerve regeneration-inducing tube by which peripheral nerve cut or excised by accident or surgical operation is reconnected utilizing the elongation of nerve cells. More particularly, the present relates to a method where close adhesion of a tubular body comprising a biodegradable and bioabsorbable polymer constituting the nerve regeneration-inducing tube with collagen applied on the outer surface of the tubular body is enhanced whereby the initial strength, flexibility, etc. of the entire nerve regeneration-inducing tube are improved.

BACKGROUND ART

There are many examples where damage of peripheral nerve caused by accident or the like is unable to be completely restored. There are also many clinical examples where peripheral nerve must be excised as a result of surgical operations in general. In the damage of peripheral nerves, autologous nerve grafting has been an only means besides a direct anastomosis. However, the result thereof is not always satisfactory but recovery of sensory perception and capacity for locomotion are bad and the aftereffect due to erroneous governing is noted as well. In addition, there are many patients complaining not only the aftereffect such as pain and deficiency in sensory perception but also the abnormal sensory perception of the diseased area or, particularly, pain.

An attempt for the regeneration of nerve by connection of gaps of peripheral nerve using a connecting tube made of artificial materials has been briskly carried out since early 1980's. However, all of the studies of connecting channels using non-absorptive synthetic artificial materials have resulted in failure. In order to solve the above, it is necessary to consider in the followings such as that invasion of connective tissues from outside is prevented during the regeneration of nerve bundles, that substance interchange inside and outside the channels or neogenesis of capillary blood vessels in channel walls is necessary, that a substance acting as a scaffold suitable for the growth of Schwann cells and axon in the channel is necessary and that, after the regeneration, the used material is degraded and absorbed. Taking those conditions into consideration, studies for artificial nerve connecting tube by a biodegradable and bioabsorbable material have been carried out thereafter.

With regard to the regeneration of peripheral nerve, attempts for extending the distance between the stumps which are able to be regenerated using a silicone tube have been conducted since a silicone tube model was reported in 1982. However, since nutrients are unable to permeate through the wall of silicone tube, there is a problem such as that the nutrients are not sufficiently provided to nerve axon whereby capillary blood vessel is unable to be produced in silicone and no satisfactory nerve regeneration has been available even when a silicone tube is used. Further, even if the nerve is able to be regenerated, there is a problem that the silicone tube which is a foreign substance anyway must be removed by means of further surgical operation, etc.

On the other hand, regeneration of peripheral nerve using a tube comprising a biodegradable polymer in place of a silicone tube has been attempted. When a nerve regeneration tube comprising a biodegradable polymer is used, the nerve regeneration tube is gradually degraded and absorbed in vivo by hydrolysis or by the action of enzymes after the nerve is regenerated whereby there is no need of taking out it by a means such as further surgical operation.

With regard to a nerve regeneration tube comprising a biodegradable polymer as such, there is a disclosure in, for example the Patent Document 1, for an auxiliary material for nerve regeneration wherein a polyester mantle in a blade form is filled with bundles of collagen fiber on which laminin and fibronectin are coated. In the Patent Document 2, there is a disclosure for an artificial nerve tube which comprises a tubular body comprising polyglycolic acid and, in the lumen of the tubular body, a collagen body having gaps and penetrating the tubular body nearly in parallel to the axial line of said tubular body where the gap is filled with a matrix gel containing collagen, laminin, etc. In the Patent Document 3, there is a disclosure for an artificial nerve tube which comprises a tubular body comprising polyglycolic acid and laminin-coated collagen fiber bundles inserted into the lumen of the tubular body nearly in parallel to the axial line of the tubular body. In the Patent Document 4, there is a disclosure for an instrument for the regeneration of biotissues or organs formed by such a manner that bundles of collagen fiber are inserted into the lumen of tubular body made of collagen together with a collagen solution. Further, in the Patent Document 5, there is a disclosure for a nerve regeneration tube where collagen is coated on and impregnated into the inner side and sponge part of a tubular body in which the inner layer has sponge of a lactic acid/ε-caprolactone copolymer while the outer layer has a reinforcing material comprising a braided rope of polylactic acid.

Those nerve regeneration tubes as such are manufactured in such a manner that a biodegradable polymer is applied on the outer surface of a tubular body prepared by using ultrafine fiber comprising a sole biodegradable polymer and a biodegradable polymer is further filled in the inner side of the tubular body. However, since the degrading speed of the biodegradable polymer which is a material for constituting the tubular body is too quick or too slow, there are problems such as that they are unable to be used for the connection of nerve with a relatively long gap (about 40 mm or longer), that the nerve regeneration tube is not degraded/absorbed but remains even after the connection of nerve and that strength, flexibility, etc. in practical use are not satisfactory.

(Patent Documents)
1. Japanese Patent Application Laid-Open (JP-A) No. 237139/93
2. WO 98/22155
3. WO 99/63908
4. Japanese Patent Application Laid-Open (JP-A) No. 2002-320630
5. Japanese Patent Application Laid-Open (JP-A) No. 2003-19196

BRIEF DESCRIPTIONS OF DRAWINGS

DISCLOSURE OF THE INVENTION

Figure 1:
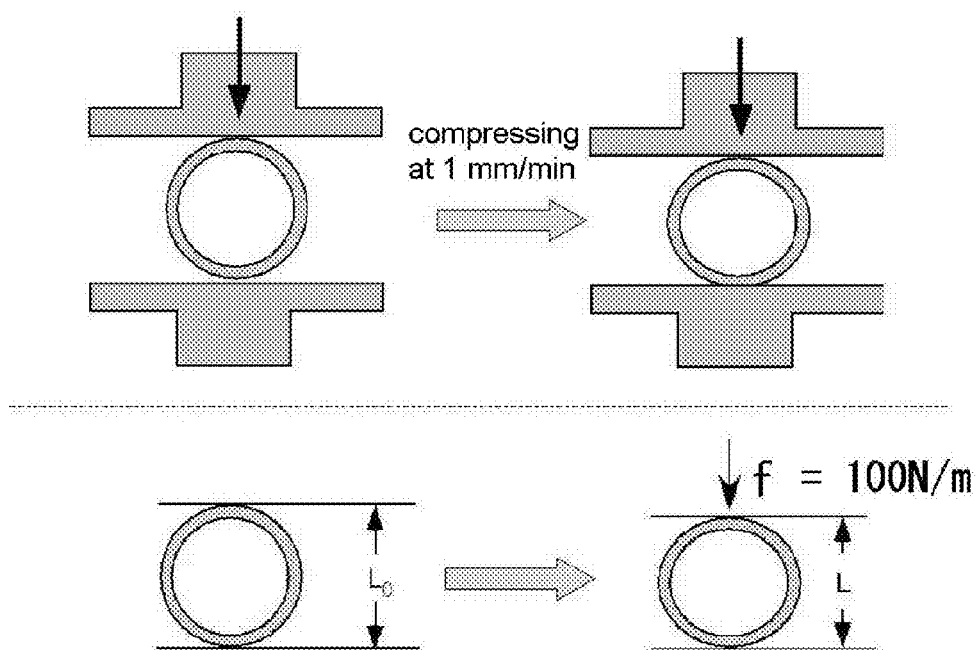
FIG. 1 is an illustrative drawing for the method of evaluation of pressure resistance.

Problem that the Invention is to Solve

The present invention has been achieved in view of the current status of the prior art as mentioned above and an object of the present invention is to provide a nerve regeneration-inducing tube being excellent in cell growth property, resistance to pressure, shape recovery property, anti-kink property and prevention of invasion of outer tissues in a nerve regeneration-inducing tube where a collagen solution is applied on the outer surface of a tubular body woven with ultrafine fiber comprising biodegradable and bioabsorbable polymer while collagen is filled in the inner area of the tubular body. A more particular object of the present invention is to provide a nerve regeneration tube where a degradation speed is adjusted so as to make it suitable for the connection of nerve gaps of more than 40 mm.

Means for Solving the Problem

In order to achieve those objects, the present inventor has conducted extensive investigations for the manufacture of a nerve regeneration tube which retards the degradation speed of a tubular body woven from a biodegradable and bioabsorbable polymer fiber and handling (shape recovery property, anti-kink property and pressure resistance) etc. are excellent and, as a result, it has been found that a nerve regeneration-inducing tube having a controlled degradability and bioabsorbability, an excellent pressure resistance, shape recovery property, anti-kink property and prevention of invasion of outer tissues is available by means of optimization of the materials for the ultrafine fiber constituting the tubular body whereupon the present invention has been achieved.

Thus, the present invention has the following constitution.

It is a nerve regeneration-inducing tube where collagen is coated on the outer surface of a tubular body woven with fiber bundles where plural ultrafine fibers comprising a biodegradable and bioabsorbable polymer are bundled, characterized in that, said tubular body mostly comprises a first polymer which is biodegradable and bioabsorbable and a second polymer which has higher biodegradability and bioabsorbability than those of the first polymer.

It is also a nerve regeneration-inducing tube wherein the biodegradable and bioabsorbable polymer is a polymer which is selected from the group consisting of aliphatic polyester, poly-ε-caprolactone or a copolymer thereof, polydioxanone, polyvinyl alcohol and bio-derived polymer.

It is also a nerve regeneration-inducing tube wherein the aliphatic polyester is a polymer which is selected from the group consisting of polyglycolic acid, polylactic acid and a lactide-glycolide copolymer.

It is also a nerve regeneration-inducing tube wherein the bio-derived polymer is selected from the group consisting of collagen, gelatin, fibronectin, laminin, chitin and chitosan.

It is also a nerve regeneration-inducing tube wherein the tubular body further contains a third polymer whose biodegradability and bioabsorbability are higher than those of the second polymer.

It is also a nerve regeneration-inducing tube wherein the third polymer is a bio-derived polymer.

Advantages of the Invention

In the nerve regeneration-inducing tube of the present invention, a tubular body is formed using two or more kinds of polymers having different biodegradable and bioabsorbable properties whereby it is now possible to provide a nerve regeneration-inducing tube having a biodegradability and bioabsorbability according to the length of the nerve gaps and also having an excellent cell growth property, pressure resistance, shape recovery property and anti-kink property.

BEST MODE FOR CARRYING OUT THE INVENTION

In accordance with the present invention, the nerve regeneration-inducing tube is able to be manufactured in such a manner that the outer surface of a tubular body woven with plural ultrafine fibers comprising a first polymer which is biodegradable and bioabsorbable and a second polymer which has higher biodegradability and bioabsorbability than those of the first polymer is coated with collagen and then collagen is filled in the lumen of the tubular body.

Inherently, living body has a self-repairing ability whereby, after its function recovers, the foreign body reaction of the living body is induced when the residential time of the material even having an excellent biocompatibility becomes long. The most important property of a biomaterial is the safety to living body and, in the case of a biodegradable and bioabsorbable material, there are demanded not only the biocompatibility of the material itself but also the safety of the degraded products. Accordingly, the material must be degraded and deteriorated in vivo either enzymatically or non-enzymatically and the resulting degraded product must be dissolved in the body fluid and then metabolized or excreted.

With regard to the biodegradable and bioabsorbable polymer constituting the tubular body, there may be exemplified aliphatic polyester, poly-ε-caprolactone or a copolymer thereof, polydioxanone, polyvinyl alcohol and bio-derived polymer. Examples of the aliphatic polyester include polyglycolic acid, polylactic acid and a lactide-glycolide copolymer. Examples of the bio-derived polymer include collagen, gelatin, fibronectin, laminin, chitin and chitosan. In view of the easy availability and handling property, it is preferred to use polyglycolic acid, polylactic acid, a lactide-glycolide copolymer, a lactide-caprolactone copolymer or collagen.

In the present invention, it is preferred to use polylactic acid, polyglycolic acid, a lactide-caprolactone copolymer or a lactide-glycolide copolymer as the first biodegradable and bioabsorbable polymer. With regard to the second polymer having higher biodegradability and bioabsorbability than those of the first polymer, it is preferred to use polyglycolic acid, a lactide-caprolactone copolymer or a lactide-glycolide copolymer. Examples of a combination of the first polymer with the second polymer in the present invention include the cases where (the first polymer/the second polymer) is polycaprolactone/polyglycolic acid, polylactic acid/polyglycolic acid, a lactide-caprolactone copolymer/polyglycolic acid, a lactide-caprolactone copolymer/a lactide-glycolide copolymer or polylactic acid/a lactide-glycolide copolymer. The case where the first polymer is a lactide-glycolide (3:97 to 34:66) copolymer and the second polymer is a lactide-glycolide (35:65 to 65:35) copolymer is also within the scope of the present invention.

With regard to the impurity contained in the artificially synthesized biodegradable and bioabsorbable polymer, there is heavy metal such as tin or phosphorus which badly affects the human body if more than a predetermined amount thereof is present in the human body. Heavy metal is used as a catalyst used in the synthesis of an aliphatic polyester, etc. The nerve regeneration-inducing tube of the present invention is retained in the living body and it is preferred to use a biodegradable and bioabsorbable polymer where the amount of heavy metal therein is, by purification treatment etc., made within such a range of being undetectable by an atomic absorption spectrometry.

When polylactic acid is used as a material for the tubular body according to the present invention, it is preferred to use polylactic acid (PLA) where the optical purity of an L-compound which is naturally present in the human body is made 99.5% or higher. Thus, with regard to polylactic acid, a lactide-glycolide copolymer or a lactide-caprolactone copolymer used in the present invention, it is preferred to use a (co)polymer containing almost no D-compound which is an optical isomer of the L-compound. Since the D-compound which is an optical isomer of the L-compound of PLA does not exist in human body, it is desirable that D-compound is not remained in the human body when safety of the human body is taken into consideration. Therefore, as to a material for the tubular body, a polylactic acid (co)polymer containing no D-compound is preferred. However, it is very difficult to artificially synthesize polylactic acid in which the optical purity of the L-compound is 100%. It is more preferred to use polylactic acid (PLA) where the optical purity of the L-compound is made 99.7% or higher.

In the present invention, the tubular body woven with fiber bundles where plural ultrafine fibers comprising the biodegradable and bioabsorbable polymer are bundled may be such a thing where each specific numbers of the ultrafine fiber comprising the first polymer and the ultrafine fiber comprising the second polymer are bundled and the resulting fiber bundles are woven or may be such a thing where ultrafine fibers are prepared by a co-dissolution of the first and the second polymers, the plurality of them are bundled and the resulting fiber bundles are woven. In the former case, the first polymer having slower biodegradability and bioabsorbability holds the shape of the tubular body even when the fiber comprising the second biodegradable polymer is firstly degraded and absorbed whereby it is possible to assist the connection of longer nerve gaps and that is preferred. In the latter case, there is an advantage that physical property and chemical characteristic of the tubular body are able to be made uniform.

In the above tubular body where each predetermined numbers of the ultrafine fiber comprising the first polymer and the ultrafine fiber comprising the second polymer are bundled and the resulting fiber bundles are woven, the ratio in bundling the ultrafine fiber comprising the first polymer and the ultrafine fiber comprising the second polymer is unable to be unconditionally mentioned since that is affected by type, molecular weight (degree of polymerization), degree of crystallization, etc. of the (co)polymer used and an example thereof is that, in case a tubular body is prepared by bundling the ultrafine fiber comprising polylactic acid (hereinafter, it may be referred to as PLA fiber) with the ultrafine fiber comprising polyglycolic acid (hereinafter, it may be referred to as PGA fiber), the ratio of the PLA fiber to the PGA fiber is preferred to be made from 2/98 to 70/30. Since the fiber such as the PLA fiber which is relatively hardly degradable and with high rigidity has a possibility of causing the damage to the surrounding tissues during its retention in the living body, it is preferred to be made a bit small amount. However, when the amount is too small, the shape of the tubular body is unable to be retained and there is a possibility of degradation and disappearance before connection of the nerve gaps takes place. Thus, the ratio of the PLA fiber to the PGA fiber is more preferred to be made from 5/95 to 60/40, and further preferred to be made from 10/90 to 55/45.

On the other hand, in case the first and the second polymers are dissolved in a common solvent, a plurality of the resulting ultrafine fibers are bundled and the resulting fiber bundles are made into a tubular body, then the compounding ratio of the first polymer to the second polymer varies depending upon the combination of the polymers used, molecular weight (degree of polymerization), degree of crystallization, etc. and may be appropriately decided depending upon the length of the nerve gaps to be connected and the site to be applied after trials and errors. An example is that, when the fiber prepared by blending of PLA and PGA is used, the mixing ratio of PLA/PGA is preferred to be from 10/90 to 70/30. As a result of blending within such a range, connection of the nerve gaps up to about 200 mm is now possible.

Another preferred embodiment of the present invention is that the tubular body further contains a third polymer where the biodegradability and bioabsorbability are higher than those of the second polymer. As to the third polymer, that derived from living body is preferred and, to be more specific, it is advantageous to use collagen, gelatin, fibronectin, laminin, chitin or chitosan. As to the third polymer, collagen is excellent among them as a scaffold for regeneration of nerve cells. Incidentally, with regard to collagen used for the manufacture of the nerve regeneration-inducing tube of the present invention including the third polymer, it is more preferred to use the collagen being subjected to a purification treatment which will be mentioned later.

When the third polymer is compounded in addition to the first and the second polymers in the present invention, said third polymer may be used as an ultrafine fiber comprising the third polymer or may be used as such a one where the first to the third polymers are dissolved in a common solvent followed by making into a fibrous form. Their compounding ratio in terms of (the first polymer)/(the second polymer)/(the third polymer) is preferred to be from (1 to 70)/(10 to 90)/(0 to 20).

When the bio-derived polymer is compounded as the third polymer, there are achieved other effects not only that the adhesive property of the nerve cells are enhanced but also that the angiogenesis is promoted whereby a preferred action is able to be resulted for the nerve growth.

The conventional collagen used as a scaffold for the nerve regeneration is usually prepared by the following manner. Thus, the pigskin collected and frozen in a meat testing factory is used as a starting material, a neutral protease is added thereto followed by warming, repeatedly washed with a sodium chloride solution, dehydrated, washed with isopropanol and acetone and dried in vacuo, the resulting defatted chip is added to an acetic acid solution, the pH is adjusted using hydrochloric acid, pepsin is added thereto to decompose, a sodium hydroxide solution is added to adjust to high pH (a virus inactivating step 1), hydrochloric acid is added to adjust to low pH (a virus inactivating step 2), the pH is adjusted to 2 to 3 using sodium hydroxide followed by filtering, a sodium chloride solution is added to the filtrate to salt out, a concentrating operation is conducted by means of centrifugal separation, the concentrated product is added to and dissolved in pure water, a sodium chloride solution is added thereto once again to salt out and the mixture is concentrated by means of centrifugal separation followed by freeze-drying.

The conventionally used collagen as such includes the steps of washing with a sodium chloride solution and salting-out using a sodium chloride solution during its manufacturing process whereby the concentration of sodium chloride in the collagen, including that which is available in the market, is 4% by weight or more. The present inventors thought that the sodium chloride concentration in the collagen affects the living and the growth of nerve cells and that, when the concentration is too high, cell membrane is destroyed due to osmotic pressure. Therefore, when collagen which is purified so as to reduce the concentration of sodium chloride contained therein is used for a nerve regeneration-inducing tube, the resulting nerve regeneration-inducing tube achieves far better cell growth ability than the one which uses the conventional collagen. On the basis of the finding as such, the present invention uses pure collagen where the concentration of sodium chloride in terms of a dry state contained therein is reduced to 2.0% by weight or less, preferably 0.1 to 1.5% by weight as a scaffold of the nerve regeneration-inducing tube. The concentration of sodium chloride is measured by means of atomic absorption spectrophotometry (by making into ash). For a purpose of prevention of destruction of cell membrane by lowering of osmotic pressure, the lower the sodium chloride concentration, the better. However, in view of technical standpoint and stability of collagen, about 0.1% by weight will be the lower limit.

(Measurement of Sodium Chloride Concentration)

Measurement of sodium chloride concentration by means of atomic absorption spectrophotometry is carried out by such a manner that 1 to 4 g of a sample is taken into a quartz beaker, carbonized by a gradual rise of temperature on an electric heater and finally made into ash by treating in a Muffle furnace for 6 to 8 hours (500° C.). The residue is re-dissolved in a 10 wt % aqueous solution of hydrochloric acid and diluted so as to make the final concentration 1 wt % and then the measurement is conducted by means of a flame atomic absorption spectrophotometry using acetylene and air. Incidentally, the measuring wavelength is 589.6 nm.

Collagen used in the nerve regeneration-inducing tube of the present invention may be produced by any of the conventionally known methods and, for example, it is able to be produced by such a manner where the conventional collagen which has been available in the market for medical use as mentioned above is used as a starting material, dissolved in distilled water for injection under cooling at 2 to 10° C., subjected to pH adjustment within a range of from 8 to lower than 9 using a sodium hydroxide solution, subjected to an isoelectric precipitation and centrifuged, the supernatant liquid is discarded and the precipitate is freeze-dried.

Although no detailed reason why the cell growth property is enhanced by the use of collagen having an isoelectric point of from 8 to lower than 9 as a scaffold for the nerve regeneration is not clear, there is a possibility that the fraction precipitated when pH is lower than 8 and 9 or higher contains a factor having low affinity to cells and, on the contrary, it is also likely that the collagen precipitated when pH is from 8 to lower than 9 has a particularly high affinity to cells. Alternatively, the unpurified collagen is constituted from type I collagen and type III collagen in a ratio of about 7:3 and there may be an influence by changing this constituting ratio of type I to type III.

The collagen which was subjected to a purification treatment as mentioned above will now be called pure collagen (IP collagen).

In the present invention, diameter of the ultrafine fiber comprising the biodegradable and bioabsorbable polymer is preferred to be from 1 to 50 μm. When the fiber diameter is too small, the fiber gap becomes dense whereby it may happen that collagen is hardly permeated into the tubular body when collagen is coated on the outer surface of the tubular body or that flexibility of the tubular body lowers. On the contrary, when the fiber diameter is too large, the retained amount of collagen becomes small whereby it may happen that the growing speed of the nerve does not rise or that the strength of the tubular body becomes insufficient. More preferably, diameter of the ultrafine fiber is 3 to 40 μm, and further preferably 6 to 30 μm.

In the formation of the tubular body, it is preferred that 5 to 60 of the ultrafine fibers comprising the biodegradable and bioabsorbable polymer and having the above fiber diameter are bundled and alternately woven as warps and woofs. When the numbers of the ultrafine fibers to be bundled are too small, it may happen that the strength of the tubular body becomes insufficient or that a sufficient retained-amount of collagen is unable to be secured. On the contrary, when the numbers of the ultrafine fibers to be bundled are too many, it may happen that a tubular body in fine diameter is unable to be prepared or that flexibility of the tubular body are unable to be secured. More preferably, the numbers of the ultrafine fibers are 10 to 50, and further preferably 20 to 40.

When a tubular body is formed by an alternate weaving of the ultrafine fiber bundles, the pore size of the network is preferred to be about 5 to 300 μm, and more preferably 10 to 200 μm. When the pore size of the network is too small, it may happen that growth of the cells and the tissues is inhibited due to the lowering of invasion of capillary blood vessel or due to the lowering of water permeability. When it is more than about 300 μm, invasion of the tissues becomes excessive whereby growth of the cells and the tissues may be inhibited.

It is preferred that although inner diameter and outer diameter of the tubular body are decided to accord with the size of the nerve to be connected and, when the production cost and the time limitation are taken into consideration, it is preferred that many kinds of tubular bodies where the sizes are varied are previously prepared. Although the size of the tubular body depends on the site of the nerve to be regenerated and on the necessary strength, it is usual that the inner diameter is 0.1 to 20 mm, the outer diameter is 0.11 to 25 mm, the film thickness is 0.05 to 5 mm and the length is 10 to 150 mm. When the film thickness is too thick, that may obstruct the regeneration of the biotissues while, when it is too thin, degradation and absorption of the tubular body are too quick whereby the shape may not be held until the regeneration of the nerve finishes. Further, when the inner diameter to the nerve to be connected is too big, there is a possibility that elongation of the nerve is unable to be done appropriately.

In the present invention, the outer surface of the tubular body is coated by applying a collagen solution for several times by a method which has been known among persons skilled in the art while the inner area (lumen) of the tubular body is filled by charging collagen therein. With regard to the collagen to be used for application to the outer surface of the tubular body and for filling into the inside of the tubular body, there may be used collagen which has been conventionally used as a scaffold for nerve regeneration. Examples thereof include type I collagen, type III collagen, and type IV collagen and the like and each of them may be used solely or plural ones may be used by mixing. With regard to the collagen, it is preferred to use a purified one where concentration of sodium chloride contained therein is made 2.0% by weight or less, preferably 0.1 to 1.5% by weight on a dry basis. The collagen may also contain laminin, heparan sulfate proteoglycan, entactin and growth factor. Examples of the growth factor include EGF (epidermal growth factor), βFGF (fibroblast growth factor), NGF (nerve growth factor), PDGF (platelet-derived growth factor), IGF-1 (insulin-like growth factor) and TGF-β (transforming growth factor). With regard to the collagen solution, it is preferred that, after every one application thereof in a form of a solution in hydrochloric acid using a brush or a writing brush, the solution is completely dried and then the next application is conducted whereby a plurality of applications are done.

When the outer surface of the tubular body is applied with a collagen solution in the present invention, it is preferred to use a low-viscosity solution of 2 to 800 cps, preferably 5 to 200 cps as a collagen solution for the first application. Frequency of the application of this low-viscosity solution is preferred to be from once to ten times, preferably once to five times. As a result of application of the low-viscosity solution of said range firstly, the collagen solution is well permeated among the ultrafine fibers of the biodegradable and bioabsorbable polymer of the tubular body whereby adhesion and unified feel of the biodegradable and bioabsorbable polymer with collagen is able to be significantly enhanced. When a high-viscosity solution having higher viscosity than the above is applied firstly, the collagen solution is unable to be permeated among the ultrafine fibers whereby the collagen becomes a filmy state after drying whereupon there is a risk that collagen is exfoliated from the tubular body. When such a nerve regeneration-inducing tube is used, there is resulted inhibition of invasion of the blood vessel into the tubular body or inhibition of growth of nerve cells.

In the present invention, it is preferred that, firstly, a low-viscosity collagen solution is applied for several times so that collagen is well permeated onto the outer surface of the tubular body and then a collagen solution of higher viscosity of 200 to 30,000 cps is applied thereon. That is because, in an application of the low-viscosity solution only, very many times of application are necessary for the formation of a collagen layer of a predetermined thickness whereby the working ability is bad. Frequency of the application of this high-viscosity solution is desired to be from once to fifty times, preferably once to thirty times. When the frequency of application of the high-viscosity solution is too many, that causes a lowering of the shape recovery property and, for example, when a diseased area is crushed with something after the surgical operation, the strain resulted on the tube is not recovered whereby it may clog the nerve regeneration path. Further, since collagen has a relatively quick biodegradation speed, there is little merit even when the application frequency is excessively increased.

Actually, it is preferred that the viscosity of the collagen solution is made higher in multiple stages of two or more after the first application of the low-viscosity solution. For example, the viscosity of the collagen solution to be applied may be raised in three stages of 2 to 200 cps, 200 to 3,000 cps and 3,000 to 30,000 cps. In that case, permeation of collagen among the ultrafine fibers of the tubular body and formation of thin film on the surface are conducted by the first low-viscosity solution, adhesion to this thin film is done using the next medium-viscosity solution to conduct the sealing of the network and the last high-viscosity solution is adhered to this sealed collagen film to enhance the strength whereby the coating with a strong initial strength is able to be efficiently carried out. Further, the gap of the viscosity applied in a stepwise manner as such is made little whereby it is possible to improve the operating ability of the applying work or to reduce the uneven application or the place left unapplied.

It is preferred that the tubular body where collagen is coated or filled is subjected to freezing, freeze-drying and cross-linking treatments to cross-link the collagen. Preferably, the freezing is carried out under the condition of −10 to −196° C. for 3 to 48 hours. As a result of the freezing, fine ice is formed among the collagen molecules and the collagen solution results in a phase separation to give sponge. After that, the above frozen collagen solution is freeze-dried in vacuo preferably at about −40 to −80° C. and preferably about 12 to 48 hours. As a result of freeze-drying, fine ice among the collagen molecules is evaporated and, at the same time, the collagen sponge becomes fine. Examples of the cross-linking method include γ-ray cross-linking, ultraviolet cross-linking, electronic ray cross-linking, thermal dehydration cross-linking, glutaraldehyde cross-linking, epoxy cross-linking and water-soluble carbodiimide cross-linking and, among them, a thermal dehydration cross-linking where the cross-linking degree is able to be easily controlled and living body is not effected even by conducting the cross-linking treatment is preferred. The thermal dehydration cross-linking is conducted in vacuo at, for example, about 105 to 150° C., more preferably about 120 to 150° C., and further preferably about 140° C. for about 6 to 24 hours, more preferably about 6 to 12 hours, and further preferably about 12 hours. When the cross-linking temperature is too high, there is a possibility that the strength of the biodegradable and bioabsorbable polymer lowers while, when it is too low, there is a possibility that no sufficient cross-linking reaction takes place.

Since the tubular body comprising the biodegradable and bioabsorbable polymer and the collagen are tightly adhered with each other in the nerve regeneration-inducing tube manufactured as mentioned above, the initial strength and elasticity which are not lower than the sum of the strength of each are available. To be more specific, in the nerve regeneration-inducing tube of the present invention, the strain rate (pressure resistance) when compression is done by applying the load of 100 N/m from the side in the direction of diameter is not more than 15%, preferably 0.1 to 10% and, further, the recovery rate (shape recovery property) in 50% of the strain when similar compression is done so as to generate of 50% strain of the tube (until the diameter of the tube becomes one half) is not less than 60%. Pressure resistance is on the assumption of the resistance to the load for the nerve regeneration-inducing tube due to the work by a medical device upon connection of nerve and to the treatment after the surgical operation and, generally, the more the thickness of the collagen layer, the more the pressure resistance. However, when the tubular body and collagen are not tightly adhered with each other but the film is separated, the pressure resistance is not able to be so much expected. In addition, the shape recovery property is on an assumption for a recovery of the shape from the strain due to the work by a medical device upon connection of nerve (such as too strong picking by a pair of tweezers) or the shock to the diseased area after the surgical operation and, if the shape recovery property is low, strain remains in the tube and the nerve growth path is inhibited.

Further, the nerve regeneration-inducing tube of the present invention has a limiting curved rate (anti-kink property) of not less than 10% and also has a high resistance to exfoliation of the film. The limiting curved rate shows the range where bending is possible without causing a kink and is an index concerning the movable region upon connection of the nerve. When the limiting curve rate is less than 10%, it is not possible to use for the case where a curved nerve growth path is necessary and, even if used, tension is applied to the nerve and there is a risk of causing the inhibition of growth of the nerve and the inflammation caused by compression of outer tissues. Resistance to exfoliation of the film is the resistance to exfoliation and crack of the coated collagen. The reason why collagen is coated on the entire outer surface of the tubular body is to prevent the invasion of outer tissue to the nerve growth path (invasion of outer tissues-prevention property) and to prevent the leakage of the collagen sponge in the inner area of the tubular body to outside (leakage resistance) and, when the coated collagen is exfoliated or cracked, there is a risk that the above properties are unable to be secured. In the nerve regeneration-inducing tube of the present invention, the tubular body and collagen are tightly adhered with each other and there is no separated film whereby a high anti-kink property is able to be achieved and, at the same time, there is no possibility that the exfoliation and the crack as such are resulted.

In the nerve regeneration-inducing tube of the present invention, a big effect is also able to be expected for the adjustment of the biodegrading and bioabsorbing rate. When a nerve regeneration-inducing tube constituted from a tubular body comprising the biodegradable and bioabsorbable polymer and collagen sponge and coated collagen is embedded in a body, the coated collagen itself disappears within one to two week(s) since the degrading rate of collagen is very high. However, when the tubular body of the present invention is used, shape and strength of the tubular body are able to be maintained for a long period since the degrading and absorbing rate of the tubular body fiber is controlled. It is an object of the present invention that the nerve regeneration-inducing tube is able to be advantageously utilized for the connection of nerve gaps of more than 40 mm and it is preferred that the tube shape in vivo is retained for more than three months. More preferably, the tube shape in vivo is retained for more than five months, and further preferably more than seven months. However, although a biodegradable and bioabsorbable polymer is used, it is still a foreign substance to living body and, therefore, inflammation reaction or the like may be resulted if it remains for too long time and it is preferred to be degraded and absorbed within one year and a half.

Further, since collagen is permeated among the gaps of the tubular body fiber, the gap is able to be sealed for a long period of time whereby it is possible to prevent the invasion of outer tissues which have a risk of inhibiting the growth of nerve cells. The reason why the degrading rate becomes slow is likely to be due to the fact that the collagen adhered to the gaps of the tubular body fibers has small contact area to the body fluid and to the outer tissues.

EXAMPLES

The effect of the nerve regeneration-inducing tube of the present invention will be shown below although the present invention is not limited thereto. Incidentally, the evaluation of the nerve regeneration-inducing tube obtained in the Examples was done in accordance with the following methods.

(1) Pressure Resistance

A load was applied at 100 N/m in a diameter direction from the side of a sample in the length of 5 mm as shown in FIG. 1 under the following measuring condition. Then, diameter height (L) in the load direction was measured whereupon a strain rate=$(L/L_0) \times 100$ (wherein, $L_0$ is a diameter height in the load direction before applying the load) was calculated. Incidentally, the sample was measured for the case of without aging and also for the case of with aging using a physiological saline solution for one, two, three and four week(s).

Measuring Condition
Temperature: 200° C.; humidity: 65.0%
Tester: Tensilon (UTA-lt).
Testing speed: 1 mm/min
Load cell rating: 5 kgf
Sample numbers: N=3

(2) Shape Recovery Property

Figure 2:
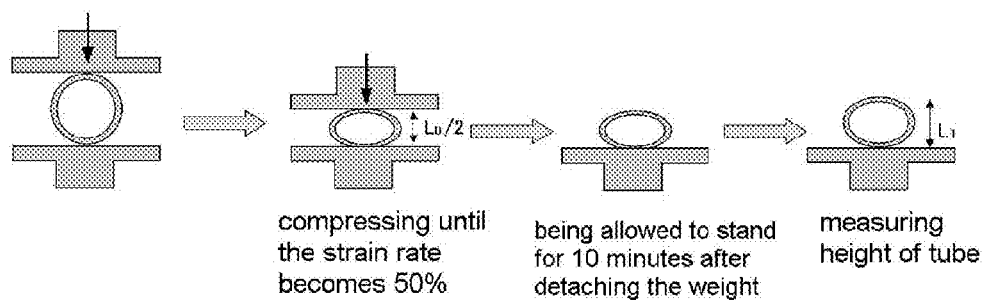
FIG. 2 is an illustrative drawing for the method of evaluation of shape recovery property.

A sample was compressed until the strain rate became 50% in the diameter direction from the side of the sample in a length of 5 mm as shown in FIG. 2 under the same measuring condition as in the above (1) pressure resistance. Immediately after the compression, the weight was detached and the sample was allowed to stand for 10 minutes. Then, diameter height ($L_1$) in the load direction was measured whereupon a shape recovery rate=$[(L_1-2/L_0)/(2/L_0)] \times 100$ (wherein, $L_0$ is a diameter height in the load direction before applying the load) was calculated.

(3) Anti-Kink Property

Figure 3:
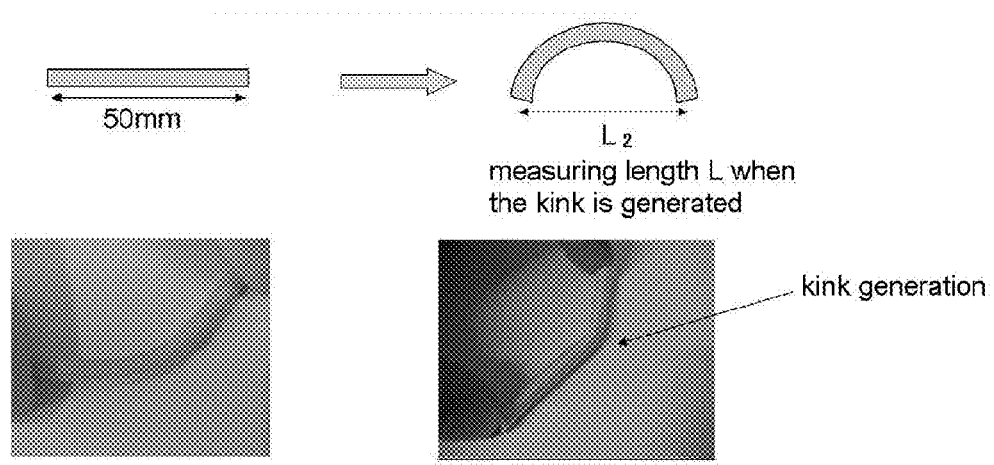
FIG. 3 is an illustrative drawing for the method of evaluation of anti-kink property.

As shown in FIG. 3, at the temperature of 20.0° C. and the humidity of 65.0%, a sample in the length of 50 mm was bent by hand at the rate of about 1 mm/second and the length ($L_2$ mm) when the kink was generated in the sample was measured whereupon a limiting curved rate $[1-(L_2/50)] \times 100$ was calculated. Incidentally, the numbers of the measured sample were made N=3.

(4) Biodegradability and Bioabsorbability

In order to check the biodegradability and bioabsorbability, each tubular body of 2 mm diameter and 10 mm length (eleven kinds of tubular bodies prepared in Examples 1 to 8 and Comparative Example 1 to 3) was hypodermically embedded into the back of each of the male rabbits (20 to 22 weeks age; body weight: 2.5 to 3.0 kg) of a white strain of Japan. The rabbits used were six in total. As to the first to the third rabbits, six kinds of tubular bodies of Examples 1 to 4 and Comparative Examples 1 to 2 were embedded to each of three rabbits. As to the fourth to the sixth rabbits, five kinds of tubular bodies of Examples 5 to 8 and Comparative Example 3 were embedded to each of three rabbits. After three months from the embedding, the first and the fourth rabbits were sacrificed and it was confirmed whether the tubular bodies were degraded. After six months, the confirmation was similarly done for the second and the fifth rabbits and, after nine months, the confirmation was similarly done for the third and the sixth rabbits. Judgment whether the degradation took place was done by naked eye. When the tubular structure was kept, it was judged to be non-degraded while, when the tubular structure was not observed, it was judged to be degraded. When degradation was noted after three months, it was marked "not more than 3 months", when degradation was noted after six months, it was marked "not more than 6 months", when degradation was noted after nine months, it was marked "not more than 9 months", and, when no degradation was noted even after nine months, it was marked "more than 9 months".

(5) Cell Growth Property

In order to confirm the cell growth property of the nerve regeneration-inducing tube of the present invention, a cell culture experiment was carried out.

(a) The prepared tubular body was dissolved in 1,1,1,3,3, 3-hexafluoroisopropanol so as to make the concentration 1% by weight, each 300 μl thereof was added to a 24-well assay plate (manufactured by Iwaki) and coating was conducted by completely drying in a drier of 60° C.

(b) P12 cells (cells derived from brown cellular tumor of adrenal gland of rat manufactured by Dainippon Pharma Laboratory Products) were previously cultured in a DMEM medium until six passages, the cells were recovered by centrifugation and suspended in 15 ml of the DMEM medium by adjusting the cell numbers to $1 \times 10^6$ and then 15 μl of NGF (a 50 μg/ml solution of cell growth factor [manufactured by R&D Systems Inc.] in a phosphate-buffered physiological saline) was added whereupon a culture liquid was prepared.

The DMEM medium is prepared by addition of 25 ml of fetal bovine serum (manufactured by Dainippon Pharma Laboratory Products), 50 ml of equine serum (manufactured by Dainippon Pharma Laboratory Products) and 5 ml of 200 mM glutamine liquid (manufactured by Dainippon Pharma Laboratory Products, 29.23 mg/ml) to 500 ml of RPMI 1640 liquid medium (manufactured by Dainippon Pharma Laboratory Products; containing no glutamic acid but containing sodium bicarbonate) followed by mixing.

(c) Each 300 μl of the prepared culture liquid was dropped into a previously-prepared well which was coated already. The well plate was incubated for four days in an incubator (30° C.; $CO_2$ concentration: 5.0%).

Figure 4:
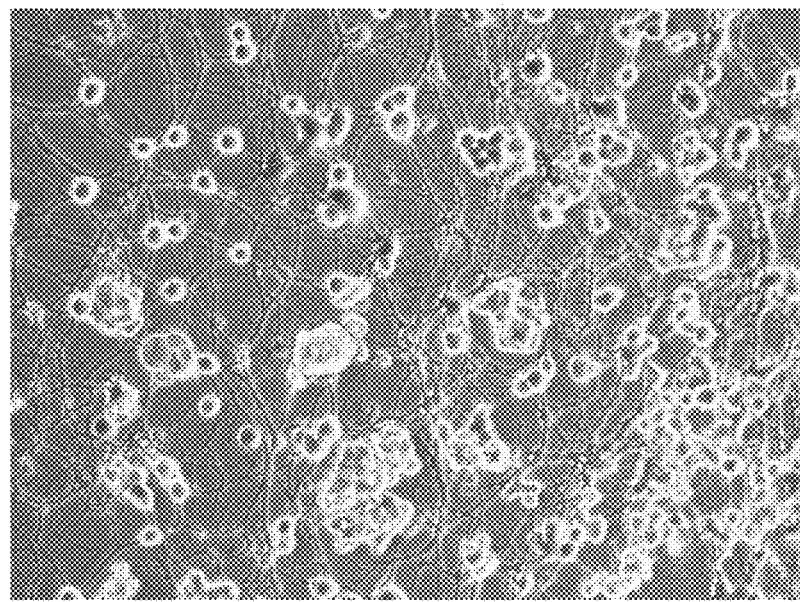
FIG. 4 is a microscopic picture showing the result of cell growth experiments using the tubular body of Example 4.
Figure 5:
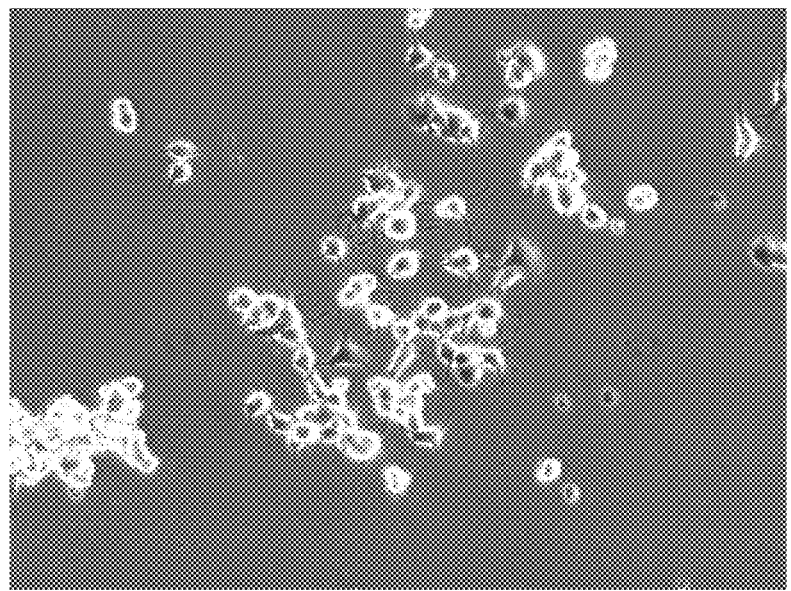
FIG. 5 is a microscopic picture showing the result of cell growth experiments using the tubular body of Comparative Example 1.

(d) After the incubation for four days, the state of the cells in the collagen gel was observed under a microscope and photographic pictures of the representative examples thereof were taken. The result is shown in FIG. 4 and FIG. 5.

Figure 6:
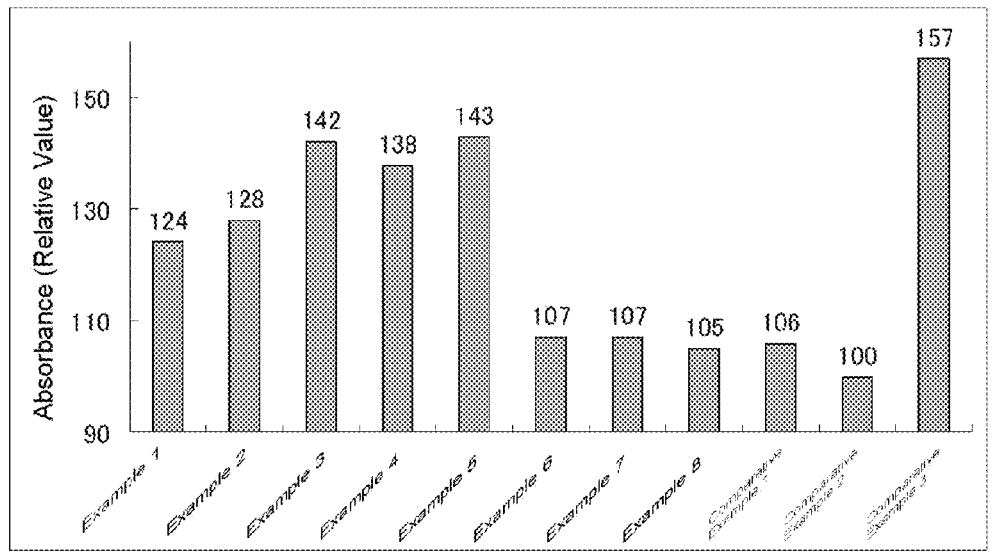
FIG. 6 is a graph showing the result of cell growth experiments.

(e) In order to measure the living cell numbers after incubating for four days, 50 μl of the MTT assay solution was added to each well and allowed to stand for 30 minutes in an incubator. After it was allowed to stand for 30 minutes, absorbance at 450 nm was measured and the value of absorbance in each well is shown in the graph of FIG. 6. In the graph of FIG. 6, the absorbance of the Examples of the present invention is expressed as a relative value when the mean absorbance of Comparative Example 2 is defined as 100. Incidentally, the absorbance is proportional to the living cell numbers.

(6) Measurement of Viscosity of Collagen Solutions

Each of the collagen solutions where collagen concentrations were 0.1, 0.2, 0.5, 0.7, 1.0 and 2.0% by weight was stabilized at the temperature of 10° C. using a constant-temperature vessel in which cooling water of 10° C. were circulated, then a B type viscometer (product name: Visco Basic plus, manufactured by FUNGILAB, rotor used: L3 spindle, measuring rotation number: 20 rpm, test number: N=3) was made to act, the measured values after 3, 4 and 5 minutes from the acting were read and the mean value thereof was adopted as a measured viscosity. The result is shown in Table 1.

Examples 1 to 8, and Comparative Examples 1 to 3

Figure 7:
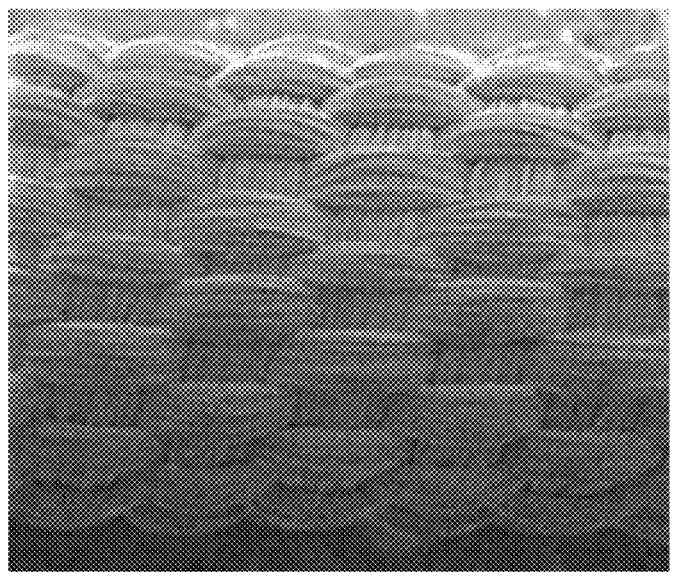
FIG. 7 shows an SEM image (50×) of the tubular body.

Fiber bundle where 28 ultrafine fibers (diameter: about 15 μm) as shown in Tables 1 and 2 were bundled was used as warp and woof and alternately woven to prepare a cylindrical tubular body of 3 mm inner diameter and 50 mm length (see FIG. 7). A collagen solution of 0.2% concentration was uniformly applied for one time on the outer surface of the resulting tubular body using a brush made of Teflon® followed by air-drying. After confirming that it was completely dried, the above collagen solution was applied once again. After that, a collagen solution of 0.5% concentration was applied thereto for three times by the same manner as above. A collagen solution of 1.0% concentration was further applied thereto for 20 times by the same manner as above. After finishing the application of the collagen solutions, a thermal cross-linking of 140° C. was conducted in vacuo (not higher than 1 Pa) for 24 hours for cross-linking the collagen molecule to prepare each of the samples of Examples 1 to 8 and Comparative Examples 1 to 3. Various evaluations were conducted using those samples. The results are shown in Tables 1 and 2.

TABLE 1

| sample No. | | Example 1 | Example 2 | Example 3 | Example 4 | Example 5 | Example 6 | Example 7 | Example 8 |
|---|---|---|---|---|---|---|---|---|---|
| method for preparation of a tubular body | | fiber bundling | blending | fiber bundling | blending | fiber bundling | blending | blending | fiber bundling |
| mixing ratio | PGA | 22 fibers | 50% | 8 fibers | 10% | 22 fibers | 30% | 90% | 14 fibers |
| | PLA | 3 fibers | 40% | 14 fibers | 70% | 1 fiber | 70% | 10% | 14 fibers |
| | collagen | 3 fibers | 10% | 6 fibers | 20% | 5 fibers | 0% | 0% | 0 fiber |
| strain at 100 N/m | without aging | 8.6% | 7.2% | 5.7% | 3.1% | 9.7% | 2.5% | 8.2% | 4.3% |
| | 1 week | 21.1% | 17.4% | 15.3% | 10.1% | 23.6% | 7.1% | 20.3% | 13.1% |
| | 2 weeks | 30.1% | 28.1% | 26.8% | 21.8% | 35.3% | 18.4% | 29.6% | 24.5% |
| | 3 weeks | 39.3% | 40.7% | 40.2% | 35.4% | 45.1% | 29.8% | 43.1% | 37.4% |
| | 4 weeks | 53.2% | 49.4% | 47.1% | 39.7% | 50.6% | 34.5% | 50.2% | 41.8% |
| shape recovery property | | 63.5% | 69.7% | 70.1% | 74.2% | 61.3% | 80.3% | 65.7% | 71.3% |
| anti-kink property | | 22.1% | 17.1% | 15.3% | 13.7% | 24.7% | 12.1% | 19.3% | 14.1% |
| biodegradability and bioabsorbability | | not more than 6 months | not more than 9 months | not more than 9 months | over 9 months | not more than 3 months | not less than 9 months | not more than 6 months | not more than 9 months |
| cell adhesion property (relative value) | | 124 | 128 | 142 | 138 | 143 | 107 | 107 | 105 |

*PGA: polyglycolic acid, PLA: polylactic acid

TABLE 2

| sample No. | | Comparative Example 1 | Comparative Example 2 | Comparative Example 3 |
|---|---|---|---|---|
| method for preparation of a tubular body | | sole | sole | sole |
| composition ratio | PGA | 100 | 0 | 0 |
| | PLA | 0 | 100 | 0 |
| | collagen | 0 | 0 | 100 |
| strain at 100 N/m | without aging | 16.2% | 2.5% | 63.1% |
| | 1 week | 35.5% | 7.1% | 70.8% |
| | 2 weeks | 52.5% | 18.4% | 79.2% |
| | 3 weeks | 64.5% | 34.5% | 83.5% |
| | 4 weeks | 66.6% | 34.5% | 89.2% |
| shape recovery property | | 42.6% | 61.2% | 29.1% |
| anti-kink property | | 3.6% | 9.1% | 2.4% |
| biodegradability and bioabsorbability | | not more than 3 months | over 9 months | not more than 3 months |
| cell adhesion property (relative value) | | 106 | 100 | 157 |

*PGA: polyglycolic acid, PLA: polylactic acid

It is apparent from the results of Tables 1 and 2 that the nerve regeneration-inducing tubes of the present invention are excellent in pressure resistance, shape recovery property, anti-kink property and cell growth property as compared with the conventional ones.

INDUSTRIAL APPLICABILITY

Since the nerve regeneration-inducing tube manufactured by the method of the present invention is excellent in the above-mentioned properties, it is excellent in the connection of nerve gaps of more than 40 mm, in the handling during the clinical use and in the stability as well as safety after the surgical operation whereby it is quite useful in the medical treatment for nerve regeneration.

The invention claimed is:

1. A nerve regeneration-inducing tube, comprising:
a tubular body comprising a plurality of fiber bundles woven together, each of said plurality of fiber bundles including a first polymer which is biodegradable and bioabsorbable and a second polymer which has higher biodegradability and bioabsorbability than the first polymer,
wherein collagen is coated on the outer surface of said tubular body,
wherein said tubular body is formed by weaving together said plurality of fiber bundles each including said first and second polymers,
wherein the fiber bundles are formed by bundling ultrafine fibers of the first polymer and ultrafine fibers of the second polymer,
wherein the first polymer is a polylactic acid and the second polymer is a polyglycolic acid, and
wherein the ultrafine fibers of the first polymer are present at a ratio of 2/98 to 70/30 relative to the ultrafine fibers of the second polymer.

2. The nerve regeneration-inducing tube according to claim 1,
wherein the tubular body further comprises a third polymer having a higher biodegradability and bioabsorbability than the second polymer, and
wherein said tubular body is formed by weaving together said plurality of fiber bundles each including said first, second and third polymers.

3. The nerve regeneration-inducing tube according to claim 2, wherein the third polymer is a bio-derived polymer.

4. The nerve regeneration-inducing tube according to claim 2,
wherein the fiber bundles are formed by bundling ultrafine fibers of the first polymer, ultrafine fibers of the second polymer and ultrafine fibers of the third polymer.

5. The nerve regeneration-inducing tube according to claim 4, wherein the third polymer is a bio-derived polymer.

6. A method of making the nerve regeneration-inducing tube of claim 1, comprising:
bundling together a plurality of ultrafine fiber bundles to form fiber bundles, the bundles comprising ultrafine fibers of the first polymer and ultrafine fibers of the second polymer, the first polymer being biodegradable and bioabsorbable, and the second polymer having higher biodegradability and bioabsorbability than the first polymer,
weaving together said fiber bundles to form a tubular body, and
coating the outer surface of said tubular body with collagen; wherein the first polymer is a polylactic acid and the second polymer is a polyglycolic acid, and wherein the ultrafine fibers of the first polymer are present at a ratio of 2/98 to 70/30 relative to the ultrafine fibers of the second polymer.

7. The method of claim 6,
wherein the fiber bundles are formed by bundling ultrafine fibers of the first polymer, ultrafine fibers of the second polymer and ultrafine fibers of a third polymer, the third polymer having a higher biodegradability and bioabsorbability than the second polymer.

8. The method according to claim 7, wherein the third polymer is a bio-derived polymer.

9. The nerve regeneration-inducing tube according to claim 1,
wherein a mixing ratio of said ultrafine fibers of the first polymer to said ultrafine fibers of the second polymer is 5/95 to 60/40.

10. The nerve regeneration-inducing tube according to claim 1,
wherein a mixing ratio of said ultrafine fibers of the first polymer to said ultrafine fibers of the second polymer is 10/90 to 55/45.

* * * * *